(12) United States Patent
Sarrut

(10) Patent No.: US 7,411,184 B2
(45) Date of Patent: Aug. 12, 2008

(54) MICROFLUIDIC DEVICE COMPRISING AN ELECTROSPRAY NOSE

(75) Inventor: Nicolas Sarrut, Seyssinet Pariset (FR)

(73) Assignees: Commissariat A l'Energie Atomique, Paris (FR); Universite des Sciences Et Technologies de Lille, Villeneuve d'Ascq (FR)

( * ) Notice: Subject to any disclaimer, the term of this patent is extended or adjusted under 35 U.S.C. 154(b) by 210 days.

(21) Appl. No.: 10/578,175

(22) PCT Filed: Nov. 9, 2004

(86) PCT No.: PCT/FR2004/050575

§ 371 (c)(1),
(2), (4) Date: May 4, 2006

(87) PCT Pub. No.: WO2005/048291

PCT Pub. Date: May 26, 2005

(65) Prior Publication Data

US 2007/0114385 A1 May 24, 2007

(30) Foreign Application Priority Data

Nov. 12, 2003 (FR) .................................. 03 50821

(51) Int. Cl.
*B01D 59/44* (2006.01)
*H01J 49/00* (2006.01)
(52) U.S. Cl. ........................ 250/288; 422/99; 422/100; 422/101; 422/102; 204/601; 239/690; 239/589; 239/691; 239/692; 137/554; 137/557

(58) Field of Classification Search ................. 250/288; 422/99, 100, 101, 102; 204/601; 239/690, 239/589, 691, 692; 137/554, 557

See application file for complete search history.

(56) References Cited

U.S. PATENT DOCUMENTS

| 5,788,166 | A | 8/1998 | Valaskovic et al. |
| 6,481,648 | B1 * | 11/2002 | Zimmermann ............... 239/690 |
| 2003/0082080 | A1 | 5/2003 | Zimmermann et al. |
| 2007/0128078 | A1 * | 6/2007 | Sarrut et al. ................... 422/99 |

FOREIGN PATENT DOCUMENTS

| DE | 100 00 691 | 7/2001 |
| WO | 98 35376 | 8/1998 |

* cited by examiner

*Primary Examiner*—Robert Kim
*Assistant Examiner*—Meenakshi S Sahu
(74) *Attorney, Agent, or Firm*—Oblon, Spivak, McClelland, Maier & Neustadt, P.C.

(57) ABSTRACT

A microfluidic device including a microfluidic chip assembled to an electrospray structure. The microfluidic chip includes at least one microfluidic channel leading through an outlet aperture to a surface area of the microfluidic chip. The electrospray structure includes at least one thin, planar point provided with a capillary slot that terminates at the end of the point so as to form an aperture for ejection of a liquid to be sprayed. The electrospray structure is arranged on the surface area of the microfluidic chip so that the point is cantilevered with respect to the microfluidic chip and so that the outlet aperture of the microfluidic device leads to the capillary slot of the point, which microfluidic device also has a mechanism to apply an electrospray voltage to the liquid to be sprayed.

9 Claims, 6 Drawing Sheets

MICROFLUIDIC DEVICE COMPRISING AN ELECTROSPRAY NOSE

TECHNICAL FIELD

This invention relates to a microfluidic device equipped with an electrospray nozzle. This type of device is intended in particular for obtaining labs-on-chip. It is used in particular in the field of mass spectrometry.

PRIOR ART

For almost ten years, various studies on the use of microfluidic chips (or labs-on chip) in mass spectrometry have been presented. This high-sensitivity detection method makes it possible to obtain information on the samples analysed (mass/charge ratio), and it makes it possible to analyse complex mixtures of molecules, when they have been separated and concentrated upstream of the analysis. Thus, one idea that has been developed is to take advantage of recent advances in microfluidics in order to integrate the sample treatments (separation, concentration, and so on) necessary for analysis by mass spectrometry.

The combination of microfluidics and mass spectrometry is usually based on a technique of electrospray ionisation or ESI of the sample. Under an intense electric field, the sample in liquid form during the pre-treatments is sprayed in an ion gas or in a multitude of charged droplets entering the mass spectrometer for analysis.

Various combination approaches have already been proposed.

In 1997, R. S. RAMSEY et al., in the article "Generating ElectroSpray from Microchip Devices Using Electroosmotic Pumping" (Anal. Chem., 1997, 69, pages 1174-1178) proposed a glass microfluidic chip of which the liquid flows are controlled by electroosmosis and of which the outlet channel opens into the wafer of the planar component. Using a positive pressure, a 12-nl drop of a sample is formed at the outlet of the chip, which drop, under an intense electric field, forms a Taylor cone by being sprayed. This approach, while simple, presents the problem of a significant dead volume of liquid (12 nl), which limits the sensitivity of the detection.

More recently, K. HUIKKO et al., in the article "Poly (dimethylsiloxane) electrospray devices fabricated with diamond-like carbon-poly (dimethylsiloxane) coated SU-8 masters" (Lab Chip, 2003; 3, pages 67-72, proposed a poly (dimethylsiloxane) (PDMS) chip also having open channels intended to be arranged opposite a mass spectrometer for spraying the sample. The authors take advantage of the hydrophobia of PDMS to obtain a small Taylor cone (limitation of the dead volume), but the PDMS technology remains a limited technology which does not yet make it possible to design complex microfluidic networks having a characteristic size on the order of one micrometer. This imposes a significant limitation on the design of microfluidic entities necessary for sample pre-treatments (concentration, separation, and so on).

Along the same technological lines as the use of polymer materials, M. SVEDERBERG et al., in the article "Sheathless Electrospray from Polymer Microchips" (Anal. Chem., 2003, 75, pages 3934-3940), and V. GOBRY et al., in the article "Microfabricated polymer injector for direct mass spectrometry coupling" (Proteomics 2002, 2, pages 405-412) proposed the integration, on a chip, of electrospray nozzles having a two- or three-dimensional shape suitable for the stability of the Taylor cone, limiting the dead volumes and integrating an output electrode necessary for the formation of the spray. The aforementioned problems remain.

Another approach consists of adapting the outlet of the separation channel so as to enable an OTC interface referred to as "PicoTip" to be received. Reference can be made concerning this topic to the article by Y. TACHIBANA et al., entitled "Robust and simple interface for microchip electrophoresis-mass spectrometry (J. of Chromatography, 1011 (2003), pages 181-192). This involves the use of a metal and/or plastic part acting as a link in the assembly of the two entities. This type of assembly has significant dead volume problems and does not solve the problem of using OTC "PicoTips" of which the dimensions are difficult to reproduce and which is very delicate to use.

Finally, U.S. Pat. No. 6,464,866 discloses a chemical analysis system produced by microtechnology, using two substrates preferably of silicon, and including a liquid chromatography system and an electrospray device. The embodiment is very complex and the integration of an output electrode appears to be an unresolved point.

DESCRIPTION OF THE INVENTION

Like the systems of the prior art, the invention proposes a device enabling microfluidics to be combined with mass spectrometry. From a technical perspective, the problem is that of assembling an electrospray nozzle having an original design, a so-called "plume"-type electrospray nozzle, to a microfluidic chip (network of channels, vessels, microreactors, micromixers, and so on) having a planar shape.

This assembly must:

comply with the conditions of operation of the electrospray (plume-type) nozzle alone, ensure a good fluidic connection between the two entities, i.e. with a minimum dead volume, integrate an electrode enabling an electric potential to be imposed on the liquid at the level of the nozzle.

The invention therefore makes it possible to produce a microfluidic device equipped with an electrospray nozzle by assembling two entities:

an electrospray nozzle produced by microtechnology techniques (in particular a "plume"-type nozzle), a planar microfluidic device.

In addition, the assembly equips the resulting device with an electrode which is an integral part of the entity obtained and located near the junction of the chip outlet channel and the electrospray nozzle.

According to the implementation selected for the assembly, the inlet of the electrospray nozzle and the outlet of the microfluidic chip will be adjusted to facilitate the assembly and allow for electrical contact between the electrode and the liquid, and minimize the dead volumes.

In addition, various simple methods for imposing an electric potential on this electrode from "the external world" will also be described.

The invention therefore relates to a microfluidic device including a microfluidic chip assembled to an electrospray structure, which microfluidic chip includes at least one microfluidic channel leading through an outlet aperture to a surface area of the microfluidic chip, wherein the electrospray structure includes at least one thin, planar point, which point is provided with a capillary slot which terminates at the end of the point so as to form an aperture for ejection of a liquid to be sprayed, wherein the electrospray structure is arranged on the surface area of the microfluidic chip so that said point is cantilevered with respect to the microfluidic chip and so that the outlet aperture of the microfluidic channel leads to the capillary slot of the point, which microfluidic device also has means for applying an electrospray voltage on the liquid to be sprayed.

The microfluidic chip is preferably assembled to the electrospray structure with adhesive.

If the adhesive is electrically conductive, the means for applying an electrospray voltage can include a layer of said adhesive which extends to the capillary slot, at the level of the outlet aperture of the microfluidic channel so as to form an electrospray electrode. In this case, the means for applying an electrospray voltage can include a contact element located on the microfluidic chip, electrically connected to the layer of adhesive and enabling an outside electrical connection.

The electrospray structure can be secured to an electrically conductive element of which a portion is arranged opposite the capillary slot, at the level of the outlet aperture of the microfluidic channel, to form an electrospray electrode. It can have a contact groove formed transversally in said structure so as to open out at the level of the outlet aperture of the microfluidic channel and expose the electrically conductive element. This electrically conductive element can be an element constituting a substrate for producing the electrospray structure.

According to another embodiment, the electrospray structure includes a leg suitable for being received in a recess of the microfluidic chip. The leg can have a groove, and the leg and recess are provided so that the groove ensures the communication of fluid between the outlet aperture of the microfluidic channel, located at the base of the recess, and the capillary slot.

BRIEF DESCRIPTION OF THE DRAWINGS

The invention can be better understood, and other advantages and special features will become clear, from the following description, given by way of a non-limiting example, accompanied by the appended drawings, in which.

DETAILED DESCRIPTION OF SPECIFIC EMBODIMENTS

Figure 1:
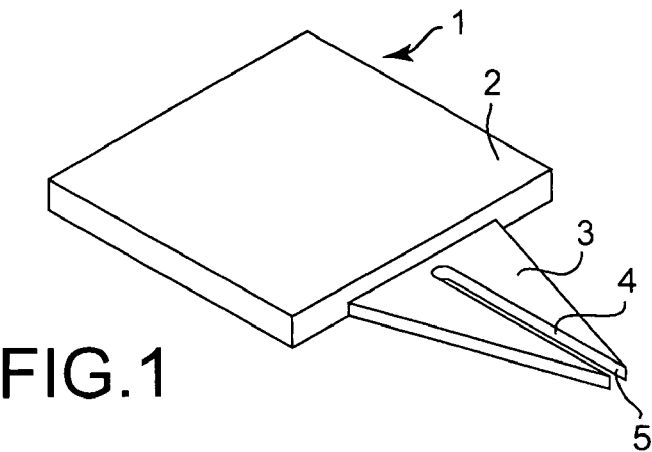
FIG. 1 is a perspective view of an electrospray structure used by the microfluidic device according to the present invention.

FIG. 1 is a perspective view of an electrospray structure (or nozzle) 1 consisting of a plate 2 extended, in the plane of one of its main surfaces, by a point 3 provided with a capillary slot 4 formed in the entire thickness of the point. The capillary slot 4 terminates at the end 5 of the point 3, intended to form an aperture for ejection of a liquid to be sprayed.

Figure 2A:
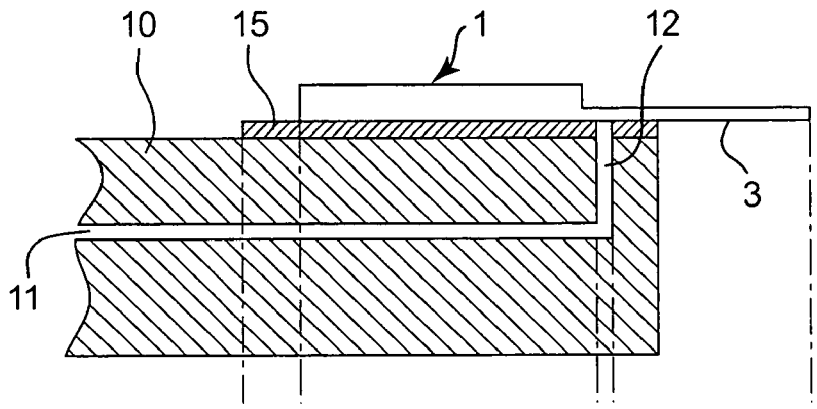
FIGS. 2A and 2B are respectively side and top views of a microfluidic device according to the present invention using the electrospray structure of FIG. 1.
Figure 2B:
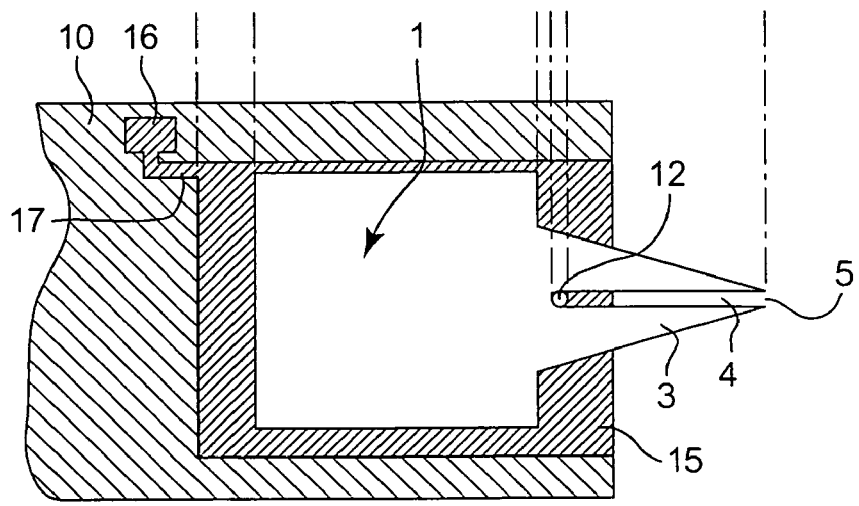

FIGS. 2A and 2B are respectively side and top views of a microfluidic device using the electrospray nozzle shown in FIG. 1.

FIGS. 2A and 2B show an assembly including a microfluidic chip 10 and the electrospray nozzle 1. The microfluidic chip 10 includes a microfluidic channel 11 leading through the outlet aperture 12 to a surface area of the microfluidic chip. The electrospray nozzle 1 is arranged on this surface area so that the point 3 is cantilevered with respect to the microfluidic chip 10 and so that the outlet aperture 12 leads to the capillary slot 4.

The outlet aperture 12 can have a diameter of between 10 and 100 µm.

According to a first embodiment, the electrospray nozzle 1 is glued to the microfluidic chip 10 using an electrically conductive adhesive 15.

To do this, the adhesive is spread on the upper surface of the microfluidic chip by printing. So as not to plug the outlet aperture 12, the adhesive must deposited in a thin layer. Adhesive printing is a technique suitable for this constraint since it enables very thin (from 1 to 10 µm) and uniform layers of adhesive to be spread (see international application WO-A-00 77509). Once the printing has been performed, the positioning and alignment of the electrospray nozzle 1 opposite the microfluidic chip 10 are ensured by a "pick and place" robot called PLATIMO (technological platform for micro-optics integration) developed by the OPUS Optics and Micro Systems company. Using optical means, the robot detects the outlet hole of the microfluidic chip (Typical diameter: from 10 to 100 µm), then detects the inlet of the electrospray nozzle (typically from 1 to 10 µm), then positions the two entities together, with micrometric precision. During this operation, the electrospray nozzle is held and moved by an arm with a suction head, while the microfluidic chip is held by a suitable support. The assembly is complete after the polymerisation of the conductive adhesive.

In this embodiment example, the electrically conductive adhesive can be TOFAY DA6524 silicone adhesive produced by DOWCORNING so as to enable an electric spray potential to be imposed on the liquid leaving the system. As shown in FIGS. 2A and 2B, once polymerised, the adhesive 15 acts as an electrode and a contact element 16 is offset from the outlet area so as to enable electrical access to the external world. This contact element 16 is itself in electrical contact with the electrode 15 (formed by the conductive adhesive) by means of an electrical lead 17. The "contact element 16/electrical lead 17/electrode 15" assembly is produced in a single conductive adhesive printing operation using a "spread cloth". This cloth, in a first step coated with adhesive, is then placed in contact with the surface to be sized, then removed, leaving a uniform film of adhesive on the surface to be used. These cloths of polymer tissue (polyester) or metal screens, sold by companies such as DUBUIS or KOENER, can be delivered with a coating of photosensitive resin. Thus, by insolation and exposure, it is easy to form on this "stencil" the complement of the "contact element/electrical lead/electrode" assembly so that only the desired area is coated with adhesive.

The electrospray nozzle and the microfluidic chip are at least partially made of electrically insulating materials so that no electrical current can circulate through their material. Thus, only the conductive adhesive can conduct the current until the liquid which appears at the outlet of the microfluidic channel of the chip and at the inlet of the electrospray nozzle.

According to a second embodiment, the electrospray nozzle is glued to the microfluidic chip using a conventional adhesive such as DELO-KATIOBOND 45952 supplied by SUPRATEC.

This assembly works in the same way as in the previous description, but in this case the electrospray nozzle must be left securely connected to its production substrate, which substrate is chosen to be electrically conductive (metal, n-type or p-type doped silicon . . . ) and which makes it possible to ensure electrical contact between the external world and the liquid appearing at the inlet of the electrospray nozzle. To do this, during the production of the electrospray nozzle, care is taken to equip it with an access to a portion of the conductive substrate (electrode) for the liquid leaving the outlet channel of the chip.

Figure 3:
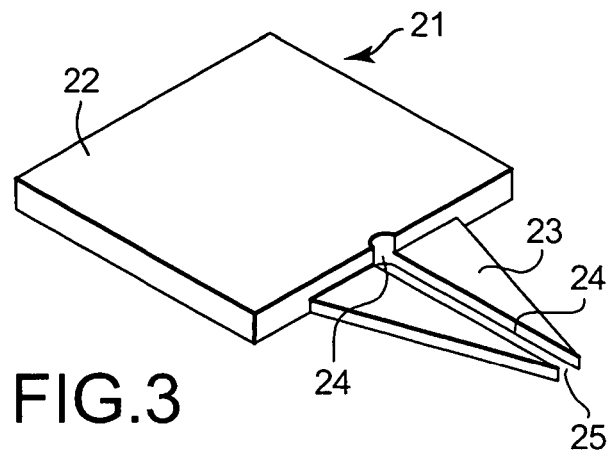
FIG. 3 is a perspective view of another electrospray structure used by the microfluidic device according to the present invention.

FIG. 3 is a perspective view of an electrospray nozzle 21 consisting of a plate 22 extended, in the plane of one of its main surfaces, by a point 23 provided with a capillary slot 24 formed in the entire thickness of the point. The capillary slot 24 terminates at the end 25 of the point 23, intended to form an aperture for ejection of a liquid to be sprayed. The electrospray nozzle of FIG. 3 is shown without its production substrate. Access to the conductive substrate portion is allowed by producing a contact groove 26 in the thickness of the electrospray nozzle. This groove, having a semi-circular cross-section in this case, can be different depending on the particular case, in particular with a rectangular cross-section. In every case, the length of this groove, which represents a dead volume for the liquid, will be minimised. In reference to the technology described below, this means minimising the thickness of the sacrificial layer (typically 200 nm), which enables the dead volumes to be reduced to negligible quantities.

Figure 4A:
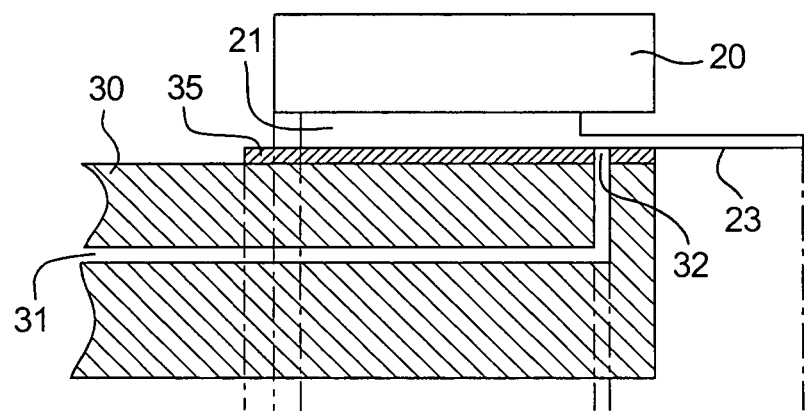
FIGS. 4A and 4B are respectively side and top views of a microfluidic device according to the present invention using the electrospray structure of FIG. 3.
Figure 4B:
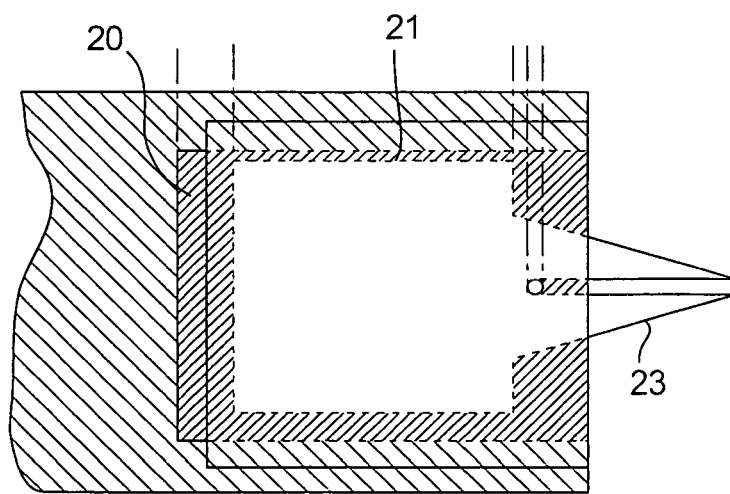

FIGS. 4A and 4B are respectively side and top views of a microfluidic device using the electrospray nozzle shown in FIG. 3.

FIGS. 4A and 4B show an assembly including a microfluidic chip 30 and the electrospray nozzle 21 secured to its conductive production substrate 20. The microfluidic chip 30 includes a microfluidic channel 31 leading through the outlet aperture 32 to a surface area of the microfluidic chip 21. The electrospray nozzle 21 is arranged on the microfluidic chip 30 as in FIGS. 2A and 2B. Reference 35 represents the conventional adhesive layer used.

According to a third embodiment, the electrospray nozzle is equipped with a leg enabling it to be inserted into the microfluidic chip. The outlet of the chip is itself suitable for the insertion of this leg, so as to guide it and to minimise the dead volumes. A contact groove passes through the leg, and, as above, the electrode consists of a conductive substrate portion secured to the electrospray nozzle. The assembly is held together by a conventional adhesive drop so as to maintain the proper position.

Figure 5:
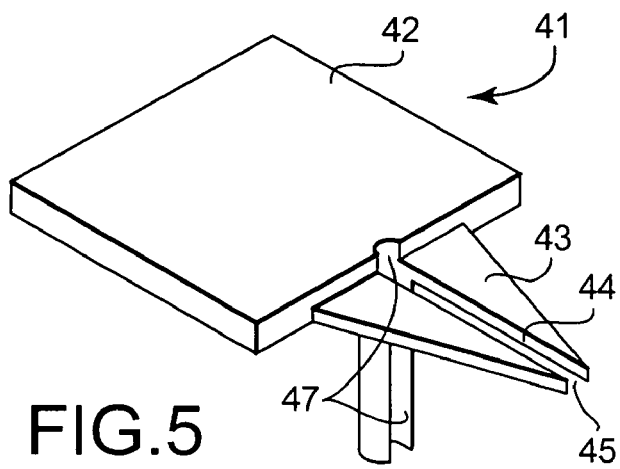
FIG. 5 is a perspective view of yet another electrospray structure used by the microfluidic device according to the present invention.

FIG. 5 is a perspective view of an electrospray nozzle 41 consisting of a plate 42 extended, in the plane of one of its main surfaces, by a point 43 provided with a capillary slot 44 formed in the entire thickness of the point. The capillary slot 44 terminates at the end 45 of the point 43, intended to form an aperture for ejection of the liquid to be sprayed. The electrospray nozzle of FIG. 5 is shown without its conductive production substrate. Reference 46 designates the leg of the electrospray structure and reference 47 represents the contact groove that will enable the passage of the liquid to be sprayed.

Figure 6:
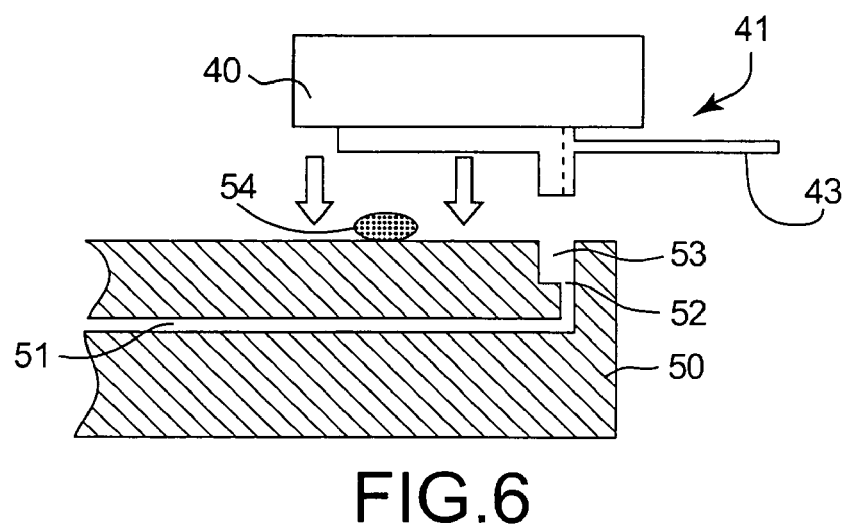
FIG. 6 is a side view showing the placement of the electrospray structure of FIG. 5 on a microfluidic chip suitable for obtaining a microfluidic device according to the invention.

FIG. 6 shows the placement of the electrospray structure of FIG. 5 on a suitable microfluidic chip. In this figure, the electrospray nozzle 41 is shown with conductive production substrate 40.

The microfluidic chip 50 includes a microfluidic channel 51 leading through an outlet aperture 52 to the base of a recess 53 which itself leads to the surface area of the chip intended to receive the electrospray nozzle. The recess 53 is intended to receive the leg 46 of the electrospray nozzle. The groove 47 is intended to ensure the communication of fluid between the aperture 52 and the capillary slot 44.

Before the placement of the electrospray nozzle, a drop of adhesive 54 is deposited on the surface area of the microfluidic chip 50.

Figure 7:
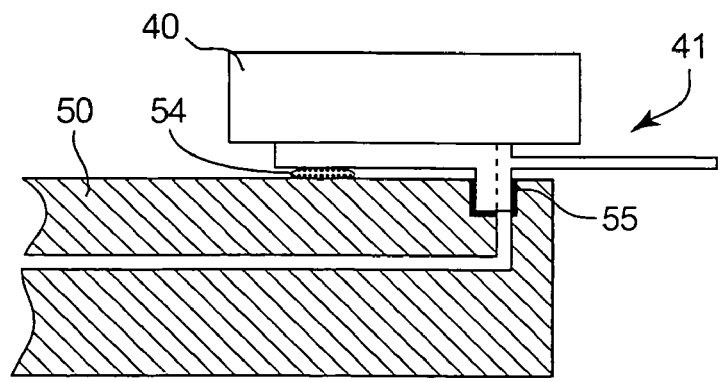
FIG. 7 is a view corresponding to FIG. 6 in which the electrospray structure is positioned on the microfluidic chip.

FIG. 7 shows the electrospray structure 41 positioned on the microfluidic chip 50 and secured to said chip by the adhesive drop 54.

Depending on the case, in particular when the pressure expected inside the component is high (hydrodynamic flow), the impermeability must be increased by the injection of adhesive between the leg 46 and the recess 53. To do this, it is sufficient to deposit a calibrated drop of adhesive. It penetrates the inside of the component by capillary action and stops at the sharp corners of the entities (areas of significant wetness). This step is not necessary when the pressure of the liquid inside the component is low, which is the case for an electroosmotic flow, always preceded by a pre-filling step.

The microfluidic device according to the invention must be electrically connected to the external environment.

Figure 8:
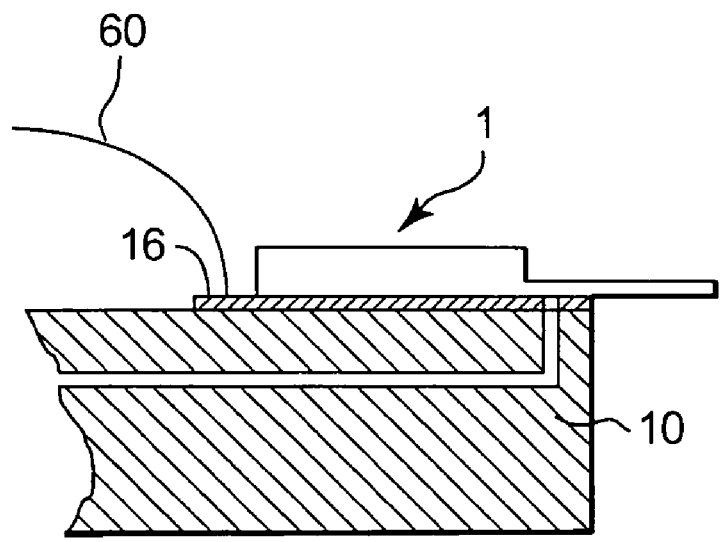
FIG. 8 shows a possibility of an electrical connection of a microfluidic device according to the invention with the external environment.

FIG. 8 shows a possibility for electrically connecting the microfluidic device shown in FIGS. 2A and 2B to the external environment.

"Wire bonding" is a conventional option for testing components produced using microtechnology and microelectronic techniques. A gold wire 60 of around 100 micrometers is welded between the contact element 16 of the device and the electrical circuit that constitutes the support of the chip. It is itself plugged in to a larger circuit in which the coaxial cables that equip OTC power supplies can be inserted.

Figure 9:
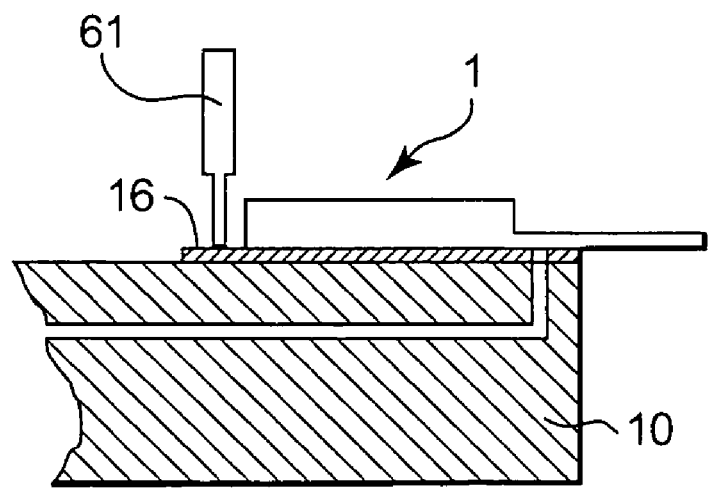
FIG. 9 shows another possibility of an electrical connection of a microfluidic device according to the invention with the external environment.

A simple contact between a gold test probe 61 and the contact element 16 (or, as the case may be, the conductive substrate) is a second solution for ensuring the connection with the external environment. This solution is shown in FIG. 9. It is easy to provide a connection between the OTC power supplies and such needles by simple welding of an electric cable. These test probes, which are spring-mounted and of which the heads are on the order of several hundred micrometers, are sold, for example, by the FM Contact Technologies company under the name Feinmetall test probes.

The microfluidic chip can be produced using two silicon or pyrex substrates having a thickness of 500 µm. The fluidic network, including the outlet channel of the chip, can be produced in a first substrate by deep etching (DRIE for "Deep Reactive Ion Etching"), then oxidised (electrical isolation of the chip). The second substrate intended to close the fluidic network of the first, can also be etched by DRIE (hole leading from the outlet channel) and thermally oxidised. Depending on the thickness of the silicon oxide layer obtained, the assembly of the two substrates is performed by anodic sealing (thin silicon oxide layer) or by direct sealing (thick silicon oxide layer, typically 3 µm).

The electrospray nozzle can be made using a thick resin such as SU8 according to a technological approach shown in FIGS. 10A to 10E.

Figure 10A:
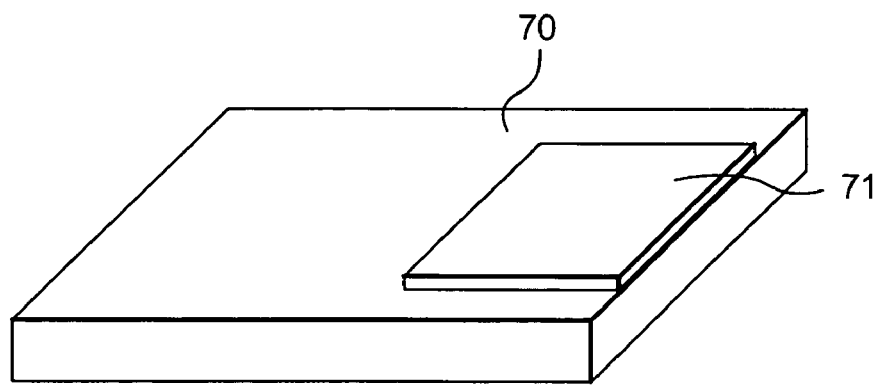
FIGS. 10A to 10E show an embodiment of an electrospray nozzle that can be used in the microfluidic device according to the invention.

FIG. 10A shows a silicon substrate 70 partially covered with a sacrificial nickel layer 71 having a thickness of several hundred nanometres. This sacrificial layer 71 is necessary for the creation of an overhang, which is itself necessary for the final cut intended to expose the electrospray nozzle.

Figure 10B:
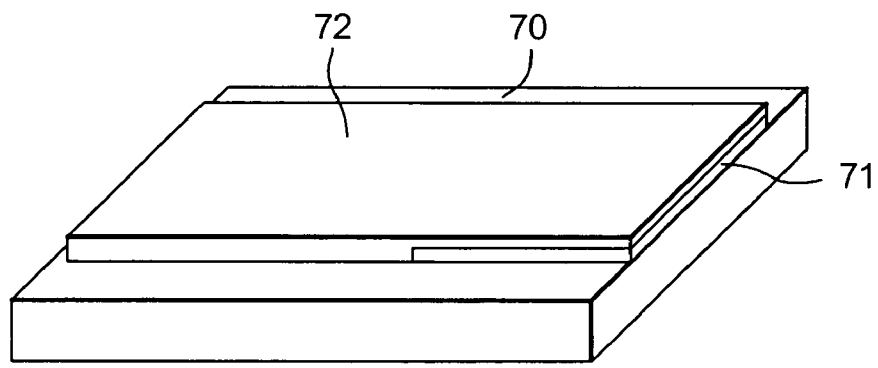

A deposit 72 of SU 8 resin, having a thickness of several dozen micrometers, is formed on the structure shown in FIG. 10A as shown in FIG. 10B.

Figure 10C:
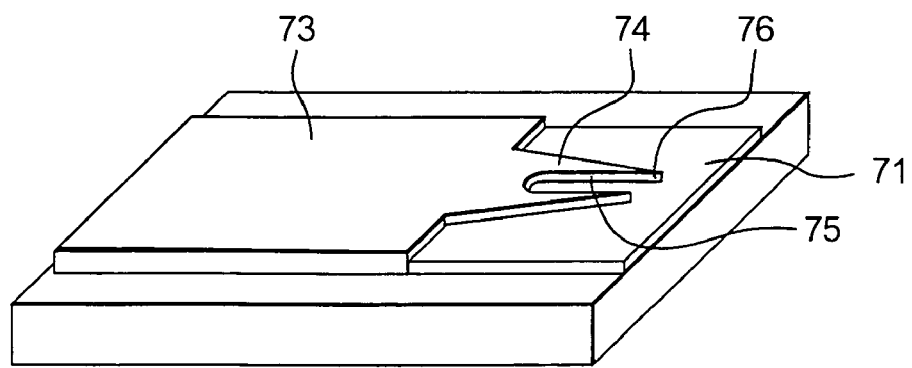

The resin deposit is then transformed by UV insolation (several dozen mW/cm$^2$) and exposure (etching of the SU 8), into a plate 73 extended by a point 74 resting on the sacrificial layer 71. This is shown by FIG. 10C. The etching also makes it possible to produce a capillary slot 75 in the point 74, which capillary slot 75 terminates at the end 76 of the point.

Figure 10D:
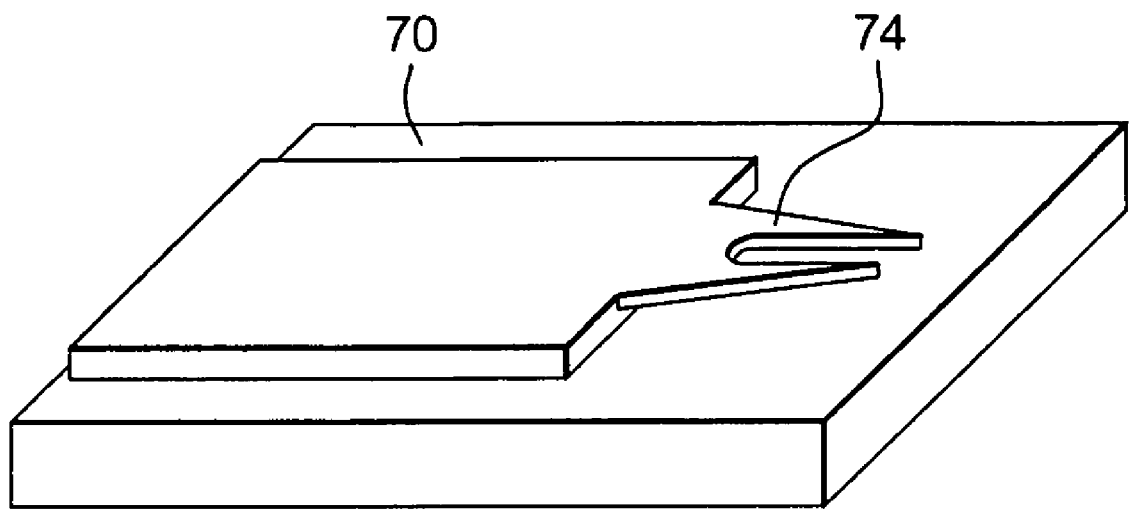

FIG. 10D shows the structure obtained after removal of the sacrificial layer. The point 74 then projects beyond the substrate 70.

Figure 10E:
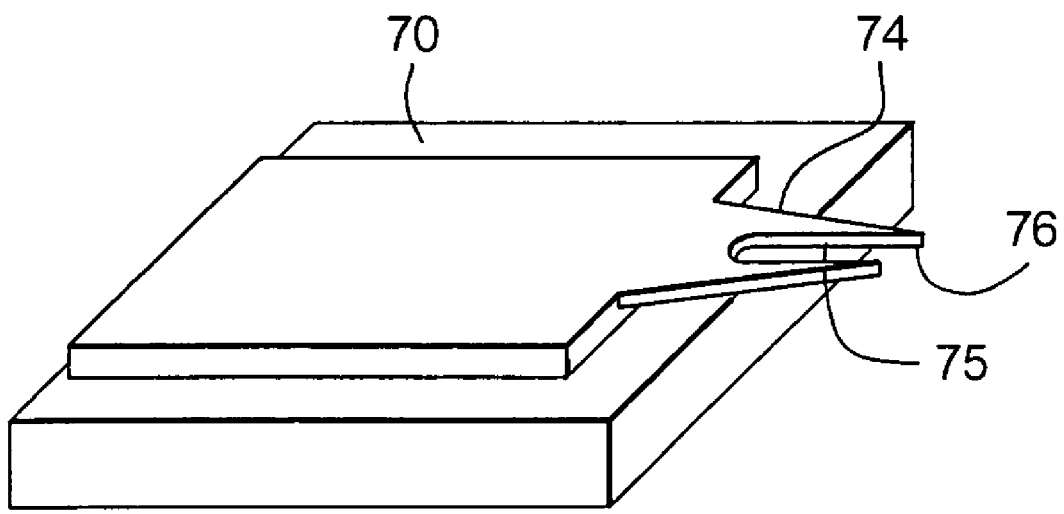

The substrate 70 is then split so as to expose the electrospray nozzle. This is shown by FIG. 10E. A portion of the point 74, a portion of the capillary slot 75 and the end 76 of the point extend beyond the substrate 70.

The invention can be used in all applications using mass spectrometry by electrospray ionisation (ESI) as the detection method.

It can be used for the analysis of samples in the biomedical field and the pharmaceutical industry:
genetic analyses,
proteomics (identification of proteins),
drug development.

The invention claimed is:

1. A microfluidic device comprising:
a microfluidic chip assembled to an electrospray structure, wherein the microfluidic chip includes at least one microfluidic channel leading through an outlet aperture to a surface area of the microfluidic chip, wherein the electrospray structure includes at least one thin, planar point, which point is provided with a capillary slot that terminates at the end of the point so as to form an aperture for ejection of a liquid to be sprayed, wherein the electrospray structure is arranged on the surface area of the microfluidic chip so that the point is cantilevered with respect to the microfluidic chip and so that the outlet aperture of the microfluidic device leads to the capillary slot of the point; and
means for applying an electrospray voltage to the liquid to be sprayed.

2. A microfluidic device according to claim 1, wherein the microfluidic chip is assembled to the electrospray structure by adhesive.

3. A microfluidic device according to claim 2, wherein the adhesive is electrically conductive, and the means for applying an electrospray voltage includes a layer of the adhesive that extends to the capillary slot, at a level of the outlet aperture of the microfluidic channel so as to form an electrospray electrode.

4. A microfluidic device according to claim 3, wherein the means for applying an electrospray voltage includes a contact element located on the microfluidic chip, electrically connected to the adhesive layer and allowing for an external electrical connection.

5. A microfluidic device according to claim 1, wherein the electrospray structure is secured to an electrically conductive element of which a portion is arranged opposite the capillary slot, at a level of the outlet aperture of the microfluidic channel, so as to form an electrospray electrode.

6. A microfluidic device according to claim 5, wherein the electrospray structure has a contact groove formed transversally in the structure so as to open out at a level of the outlet aperture of the microfluidic channel and expose the electrically conductive element.

7. A microfluidic device according to claim 5, wherein the electrically conductive element is an element constituting a substrate for producing the electrospray structure.

8. A microfluidic device according to claim 7, wherein the electrospray structure includes a leg configured to be received in a recess of the microfluidic chip.

9. A microfluidic device according to claim 8, wherein the leg includes a groove, and the leg and the recess are arranged so that the groove ensures communication of fluid between the outlet aperture of the microfluidic channel, located at a base of the recess, and the capillary slot.

* * * * *